(12) United States Patent
Dähne et al.

(10) Patent No.: US 9,682,203 B2
(45) Date of Patent: Jun. 20, 2017

(54) INHALER SYSTEM FOR VOLATILE SUBSTANCES

(75) Inventors: Lars Dähne, Berlin (DE); Gabriella Egri, Berlin (DE); Claudia Aldenhoven, Berlin (DE)

(73) Assignee: SURFLAY NANOTEC GMBH, Berlin (DE)

( * ) Notice: Subject to any disclaimer, the term of this patent is extended or adjusted under 35 U.S.C. 154(b) by 1349 days.

(21) Appl. No.: 13/521,568

(22) PCT Filed: Jan. 10, 2011

(86) PCT No.: PCT/EP2011/050232
§ 371 (c)(1),
(2), (4) Date: Nov. 7, 2012

(87) PCT Pub. No.: WO2011/083168
PCT Pub. Date: Jul. 14, 2011

(65) Prior Publication Data
US 2013/0047984 A1 Feb. 28, 2013

(30) Foreign Application Priority Data
Jan. 11, 2010 (DE) .......... 10 2010 000 043

(51) Int. Cl.
*A61M 15/06* (2006.01)
*A61K 9/00* (2006.01)

(52) U.S. Cl.
CPC .......... *A61M 15/06* (2013.01); *A61K 9/007* (2013.01)

(58) Field of Classification Search
CPC ........ A24F 47/002; A24F 47/008; A24F 1/00; A24F 47/004; A61K 48/0008; A61K 9/0024; A61K 9/007; A61K 9/1647; A61K 9/1652; A61K 9/1658; A61K 9/1694; A61K 9/5073; A61K 9/5078; A61K 9/5153; A61K 9/5161; A61K 9/5169; A61K 9/70;
(Continued)

(56) References Cited

U.S. PATENT DOCUMENTS 6,286,516 B1 * 9/2001 Bowen .............. A24D 1/02
131/331
8,286,642 B2 * 10/2012 Woodson ........... A24D 1/00
131/274
(Continued)

FOREIGN PATENT DOCUMENTS

AT         505472 A1    1/2009
DE    10200401367 A1   10/2005
(Continued)

OTHER PUBLICATIONS

Routine Analytical Cigarette-Smoking Machine Definitions and standard conditions (IS 3308: 2000) Dec. 2000.

*Primary Examiner* — Annette Dixon
(74) *Attorney, Agent, or Firm* — Yankwich & Associates, P.C.; Leon R. Yankwich; Michael R. Wesolowski (57) ABSTRACT

The invention relates to a depot for storing and dispensing a substance into a gas phase, having a hybrid structure made of an open-pored macroporous support skeleton, through which a gas can flow, and nanoporous particles immobilized on the support skeleton, which in the pores thereof contain at least one active ingredient to be released, wherein the support skeleton consists of particles or fibers that are permanently connected to each other.

11 Claims, 9 Drawing Sheets

(58) Field of Classification Search
CPC ......... A61L 2300/252; A61L 2300/258; A61L 2300/43; A61L 2300/602; A61L 2300/622; A61L 2300/624; A61L 27/54; A61L 27/56; A61M 15/0003; A61M 15/0028; A61M 15/06; A61M 16/107; A61M 2205/3613; B01J 13/02; Y10T 428/2991; Y10T 82/13; Y10T 82/2502; Y10T 82/2533; A24D 1/14; G05B 19/184; G05B 2219/37611; G05B 2219/45218; G05B 2219/50053
USPC ............ 128/203.12; 131/274, 329, 194, 195, 131/196, 226, 273, 336, 359; 424/443, 424/490
See application file for complete search history.

(56) References Cited

U.S. PATENT DOCUMENTS

| | | | | |
|---|---|---|---|---|
| 2005/0133049 A1* | 6/2005 | Fournier | ................ | A24D 3/166 131/207 |
| 2006/0225753 A1* | 10/2006 | Kaczmarek | .......... | A24B 15/282 131/334 |
| 2006/0246121 A1* | 11/2006 | Ma | ....................... | A61K 9/0024 424/443 |
| 2008/0020051 A1 | 1/2008 | Dahne et al. | | |
| 2010/0059073 A1 | 3/2010 | Hoffmann et al. | | |
| 2014/0246033 A1* | 9/2014 | Daehne | ................. | A24F 47/002 131/329 |

FOREIGN PATENT DOCUMENTS

| | | |
|---|---|---|
| DE | 10356925 B4 | 5/2006 |
| DE | 102005054255 A1 | 5/2007 |
| DE | 202007004678 U1 | 9/2007 |
| DE | 102008014587 A1 | 4/2009 |
| WO | WO 2004/095955 A1 | 11/2004 |
| WO | WO 2004/098324 A2 | 11/2004 |
| WO | WO 2006/002455 A2 | 1/2006 |
| WO | WO 2008/113335 A2 | 9/2008 |
| WO | WO 2009/105919 A1 | 9/2009 |

\* cited by examiner

INHALER SYSTEM FOR VOLATILE SUBSTANCES

CROSS-REFERENCE TO RELATED APPLICATIONS

This application is a United States national stage filing under 35 U.S.C. §371 of international (PCT) application no. PCT/EP2011/050232, filed Jan. 10, 2011, and designating the US, which claims priority to German (DE) Appln. No. 10 2010 000 043.4, filed Jan. 11, 2010.

FIELD OF THE INVENTION

The present disclosure relates to a depot (or repository) for storing volatile substances, for example active substances and flavouring agents, to an inhaler system for the release of volatile active substances and flavouring agents from said depot, and to the use of the depot, for example to accommodate or administer stimulants, wellbeing-enhancing substances, pharmaceuticals, pesticides or flavouring agents.

BACKGROUND OF THE INVENTION

Devices resembling cigarettes consisting of a filter with a nicotine depot are described in WO 2004/098324, WO 2004/095955, WO 2009/105919, DE 10 2008 014 587, DE 10 2005 054 255 A1, DE 103 56 925 B4, WO 2006/002 445 A2 and AT 505 472 A1.

SUMMARY OF THE INVENTION

With this prior art as the background, a depot (or repository) for storing and releasing a substance into a gas phase, comprising a hybrid structure formed from: an open-pored macroporous support matrix through which a gas can flow; and nanoporous particles immobilized on the support matrix which contain at least one releasable substance in their pores; wherein the support matrix is comprised of permanently interconnected particles or fibres; or a depot for storing and releasing a substance into a gas phase, comprising a hybrid structure formed from: an open-pored macroporous support matrix through which a gas can flow; and nanopores formed in the material of the support matrix; wherein the support matrix substantially consists of an inorganic material such as glass, silicates or aluminosilicates and wherein the pores contain at least one substance to be released, is proposed. Further, a cartridge is proposed for a dosing device as follows: a cartridge for a dosing device, comprising: a cylinder, wherein the cylinder has at least one inlet opening and at least one outlet opening; a depot as recited above, wherein the depot is held in the cylinder between the inlet and outlet opening. Further, a smokeless cigarette, cigarillo, cigar or tobacco pipe comprising a base unit and at least one depot as recited above disposed in the base unit, wherein the substance is nicotine, a nicotine salt, a nicotine derivative or a component of cigar or cigarette tobacco, which is adsorbed onto or fixed in the pores is proposed. Furthermore, a device for the discontinuous or continuous release of a substance with a gas stream is proposed as follows: a device adapted to release a substance into a stream of gas, comprising a depot as recited above or a cartridge as recited above, wherein the stream of gas can be conducted through the depot. Further, the use of a depot or a cartridge is proposed. Methods for the manufacture of a depot are also proposed. Further embodiments and advantages will become apparent from the dependent claims, the description below and the figures.

BRIEF DESCRIPTION OF THE DRAWINGS

The present invention will now be explained in more detail with the aid of the figures, in which:

FIG. 1A-C diagrammatically shows the construction of a depot (hybrid depot); FIG. 1A shows a macroporous support matrix formed from sintered particles (1). The rectangle shown in dashed lines (4) diagrammatically shows a sectional plane through this sintered support matrix. FIG. 1B diagrammatically shows an enlarged view of the section (4) through the support matrix shown in FIG. 1A. Reference numeral (2) therein shows the pores, cavities and interstitial spaces of the particles (1) forming the support matrix. These pores, cavities and interstitial spaces (2) form a through network in which the nanoporous particles (3) are stably and permanently embedded or attached. FIG. 1C is a diagrammatic detailed view of a section through such a nanoporous particle (3). The nanoporous particle has pores (5) in the range 1 to 900 nm. At the surface of the nanoporous particles, in particular on the inner surface of the nanoporous particles formed by the pore walls, the active substance or flavouring agent (6) is adsorbed and is in constant exchange with the gas diffusing or flowing through the particle.

FIG. 4A-B shows a microscope image of a macroporous depot (Example 2)

FIG. 5A-B shows the nicotine release from the depot of Example 5.

FIG. 6A-B shows the nicotine release from the depot of Example 6; FIG. 6A shows individual measurements; FIG. 6B shows the cumulative release. The line drawn through them (square data points) shows the measured release of nicotine for a nicotine load of 10 mg through unmodified nanoporous particles. The dashed line (circular data points) shows the measured release of nicotine for a load of 10 mg of nicotine through particles with pores coated with poly (allylamine) (PAH) and then with poly(methacrylic acid) (PMAA). The dotted line (triangular data points) shows the path of the measured release of nicotine after increasing the affinity of the nanoporous particles for nicotine using the LbL coating described in Example 6 with poly(allylamine)/poly(styrene sulphonate) for a 10 mg nicotine charge.

FIG. 7(1-2) compares depots after manufacture and storage (Example 7); FIG. 7(1) shows the samples immediately after loading with nicotine. FIG. 7(2) shows the depots after storing under the given stress conditions, which were comparable with storing at room temperature for several months.

FIG. 8A-B shows the nicotine release from the depot of Example 9.

FIG. 9A-B shows the nicotine release from a depot according to Example 10.

DETAILED DESCRIPTION OF THE INVENTION

In the search for a depot for active substances or flavouring agents to release them into a gas stream, it was surprisingly discovered that hybrid materials formed by a combination of a macroporous support matrix with nanoporous storage particles permanently attached thereto are highly suitable.

The technical advantages of the embodiments described here lie in the preparation of a filter-like active substance depot for an inhaler system, for example for a smokeless cigarette, a smokeless cigarillo, a smokeless cigar or a smokeless tobacco pipe and in the administration by inhalation of the wellbeing-enhancing substance or mixture of substances. The air resistance of the active substance depot, for example in the form of a filter, can thus be low without other substances or particles apart from the desired active substances and flavouring agents being released. The term "smokeless cigarette" as used below also encompasses a smokeless cigarillo, a smokeless cigar or a smokeless tobacco pipe. The term "smokeless" as used here means that the tobacco or similar tobacco product is not burned.

Further technical advantages of the described embodiments are to be found in the provision of a dosing system, for example in the form of a depot, for controlled release of active substances and/or flavouring agents into the air, for example into the air of enclosed spaces. The material stored in the active substance depot can be released over a given time period in prescribed quantities by passage of a gas or gas mixture.

The enclosed space may in particular be one of the following: store rooms, for example for protected storage of museum pieces; storage and silos for storing harvested goods, seeds and plant material (stored produce); greenhouses, for example for ornamental plants and market gardening; other agricultural storerooms and storerooms for the food industry, or small enclosed chambers and containers with controlled humidity and/or controlled temperatures. Typically, substances for these applications which may be considered are active substances or mixtures of active substances which are biologically active, for example with insecticidal or acaricidal effect. Examples of substances of this type are cinerin, jasmolin and pyrethrin, and also other pyrethroids. Depots containing these substances may advantageously be combined directly with substances having a synergistic effect, for example with piperonyl butoxide, or with depots containing these synergistic substances. Another example of an active substance is p-menthane diol. Rodenticides may also be introduced into the depot, or be selectively released from the depot.

It is also possible to use them in applications for spaces with particular hygiene requirements as regards cleanliness or fragrance, such as (public) toilets, baths, swimming baths, showers, sports halls and gymnasiums, fitness centres, saunas, etc.

According to one or more embodiments, the depot may be used directly or as a component of a dosing system for local release of substances into the air. A typical use in this regard is the release of repellents, for example for forest management to protect against damage from game. When released, the active substance or mixture of substances stored in the depot frightens off game that could cause damage in the wild, in forests, nurseries, tree nurseries, or gardens and parks. According to one or more embodiments, the depot or the dosing system may be used with these repellents to deter pets from buildings or areas, for example along land boundaries.

According to one or more embodiments concern the use of depots to release insect repellents to protect against annoying insects, for example in rooms or open areas or gardens. A number of other embodiments concern the deliberate release of pheromones for specific use in the integrated protection of plants from insect pests, for example using pheromone traps.

According to one or more embodiments concern a hybrid material for an active substance depot, which combines various functions in one filter system. As an example, an open-pored material with pore widths in the micrometer range (also known as macropores), which allow air to pass through without great resistance, may be combined with nanoporous particles. Further, the nanoporous particles can be permanently attached to the surface of an open-pored support matrix. The quantity and size of the nanoporous particles are selected such that on the one hand the macropores are not blocked and on the other hand they can adsorb sufficient active substance into the interior of the particles. The active substances and flavouring agents are, for example, adsorbed inside the nanoporous particles. In particular, the active substances and flavouring agents are directly available, i.e. not dissolved in a solvent. It has been shown that solvent-free adsorption is beneficial for subsequent release of the active substances and flavouring agents. In a number of embodiments, the support matrix can be constructed from particles, fibres, particulate material or mixtures formed from these materials. The particulate material or mixture of materials can, for example, be sintered, fused, bonded or otherwise interconnected so that a mechanically stable open-pored support matrix is produced.

According to one or more embodiments, the support matrix can also consist of a loose fill of particulate material or a mixture of materials, whereby the support matrix is present in a suitable container.

According to one or more embodiments, the substances fixed in or adsorbed on the hybrid material are released into the gas flow by convection and/or diffusion. The preferred structural features of the depot, for example the support matrix, result from the preferred release rates for the substance or substances present in the depot for the respective application.

According to one or more embodiments, a depot for storage and release of a substance into the gas phase may be a hybrid structure, which is formed from an open-pored macroporous support matrix with channels through which a gas can easily flow, and of immobilized, nanoporous particles which contain the active substance to be released in pores with nanometer dimensions and which are interconnected via the channels of the support matrix, whereby the support matrix consists of permanently interconnected particles or fibres. As an example, the channels have a mean width which in total permits a gas to flow through. As an example, the channel width (for example diameter, if the channels have an approximately circular cross section) may be in the region of a few hundred micrometers, for example in the range 100 μm to 800 μm. Clearly, it will be understood that this refers to a mean channel width since the channels may have an irregular shape and also there may be a distribution of channel sizes.

According to one or more embodiments, the microparticles used to form the support matrix may have dimensions of 200 to 1000 μm. Nanoporous particles may be permanently fixed to the surface of the pores formed by sintering, for example. According to one or more embodiments, the open-pored support matrix has macropores that are larger than the nanoporous particles, which act to take up the active substance or the flavouring agent. According to one or more embodiments, the dimensions of the macropores present in the support matrix are typically in the range 10 μm to 800 μm, for example in the range 20 μm to 700 μm, in particular in the range 25 μm to 600 μm.

According to one or more embodiments, said nanoporous particles, typically have particle diameters of 5 μm to 500 μm, for example diameters in the range 10 μm to 300 μm, in particular diameters in the range 20 μm to 150 μm. Typically, their nanopores are in the range 1 nm to 900 nm; as an example, their pore diameters are in the range 3 nm to 700 nm, in particular in the range 6 nm to 500 nm. The nanopores formed in the support matrix may also be in the same size range.

According to one or more embodiments, the nanoporous particles are mixed together with the particulate material (microparticles, fibres or the like) and then the particulate material is interconnected to form an open-pored support matrix, whereupon the nanoporous particles are simultaneously immobilized in or on the support matrix.

In accordance with a number of embodiments, in comparison with the material from which the support matrix is formed or in comparison with particles from which the support matrix is formed, the nanoporous particles have a higher melting point. This ensures that on heat treatment to consolidate the support matrix, the nanoporous particles do not melt or their pores do not stick together. The nanoporous particles can thus become "embedded" in the surface of the support matrix particles by softening.

In various embodiments, particle or fibre-shaped sintered materials formed from inorganic materials such as silicates or aluminosilicates are used to form the macroporous support matrix of the depot. In addition, organic polymers may also be used for the macroporous support matrix, such as polyethylene or polypropylene, polyvinyl chloride, polycarbonate, polyester and other materials. When used for inhalers, care should be taken that the polymers do not contain softeners. In the case of particulate sintered materials, the particle size should be selected such that air can easily pass through the desired length of the depot.

According to one or more embodiments, the depot may be formed from a mixture of support particles or fibres of different sizes, or from particles of different materials. In addition, different nanoporous particles which differ in size and/or shape and/or pore size and/or material and/or affinity with the active substance may be embedded in the support matrix at the same time. The particles used to produce the depot may also be a mixture of differently charged porous particles or be porous particles loaded with different substances.

According to one or more embodiments, the size and shape of the depots is matched to the respective application. In particular, it is adapted to the geometry of the inhalation or dosing system. As an example, the depot may be formed as a cartridge for accommodation in a head or shaft of a conventional tobacco pipe, or it may have the size, shape and colour of a cigarette filter or it may be prepared as an insert in an imitation cigar or cigarillo. If the dosing system is to be used in the agricultural field or warehousing field, the depot is prepared and adapted to the prospective release of the respective active substance. With adapting, a good accessibility to the nanopores for the passing gas or air stream and even distribution of the substances are obtained.

In this regard, the shape of the depot and/or the cartridge may advantageously be cylindrical or even be angular, such as cubic or rectangular. According to one or more embodiments, the depot is in an exchangeable filter stick for a smokeless cigarette. In a number of embodiments, the smokeless cigarette can be formed without an additional source of heat. In this case, the gas or air stream that is drawn in is approximately at ambient temperature. According to one or more embodiments, the smokeless cigarette may have a source of heat in order to heat the gas stream that has been drawn in. According to one or more embodiments, the depot may be in the form of a filter disk or a filter depot.

According to one or more embodiments, a smokeless cigarette, cigarillo, cigar or tobacco pipe is provided having a base unit with a receptacle to accommodate a depot, wherein the substance is nicotine, a nicotine salt or a component of cigar or cigarette tobacco which is adsorbed onto or bound in the nanopores.

As an example, depending on the purpose, the height (length) and width (diameter) of a macroporous cylindrical support matrix can be adjusted depending on the volatility of the active substance, the temperature of the incoming stream of air, the desired concentration of the gas stream leaving the depot, the load, the flow resistance, and also the quantity of nanoporous particles to be immobilized.

Surprisingly, inorganic adsorbents with as large an internal surface area as possible are suitable nanoporous depot materials for active substances and flavouring agents. The internal surface area of the adsorbents is formed by the walls of the pores, so a large contact area is available for substances that can enter the pores. In addition to porous aluminosilicates, nanoporous silicates are particularly good for taking up active substances such as p-menthane diol, menthol, salbutamol or nicotine.

These adsorbents have an open-pored network of interconnecting tubes. They are commercially available with predetermined mean pore sizes, usually with pore diameters of 3 nm, 7 nm, 12 nm, 30 nm and 100 nm, as chromatographic support materials. However, it is also possible to use broader pore distributions in the nanometer range, such as 3 nm to 700 nm.

The particle size of suitable nanoporous materials is, for example, in the range 10 μm to 1 mm, in particular in the range 50 μm to 700 μm. The nanoporous materials may have a spherical shape. In accordance with one embodiment, irregular broken materials and thus irregularly shaped particles are used for embedding.

According to one or more embodiments, the active substance or flavouring agent is nicotine or a nicotine derivative. At room temperature, the active substance nicotine forms a colourless liquid which is frequently already slightly yellow due to the onset of oxidation. Nicotine has a relatively high boiling point of 246° C., so that at lower temperatures, the saturation concentration of nicotine in air drops severely. Nicotine is prone to oxidation with oxygen of the air, so in contact with it, it decomposes to a dark brown coloured compound. According to one or more embodiments, two depots may be combined together with different substances adsorbed in each one. As an example, one of the substances may be intended to partially or completely modify the other substance, for example by chemical transformation. As an example, one substance may be nicotine which with another substance, for example an acid, is transformed at least in part into a nicotine salt in order to improve the compatibility (tolerability) of the inhaled nicotine. Thus, the acid is contained in the "upstream" depot. The filter stick for smokeless cigarettes or a cartridge for a dosing device can thus have at least one depot. According to one or more embodiments, the filter stick and the cartridge may have at least two depots arranged one behind the other in the direction of gas flow.

Tests on the long-term stability of nicotine in the described depot compared with the usual support materials such as acetate fibres showed a substantially reduced yellow or brown colouration. Compared with nicotine in an adsorbent support, for example acetate fibres, the nicotine present in the nanoporous particles is more stable as regards oxidation in air. This is remarkable, since the contact surface area with air in the nanoporous particles is very large. Without wishing to be bound thereby, it is postulated that the sensitivity of nicotine to oxidation of the nanoporous material when adsorbed on the surface, for example the internal and external surface of silica particles, is considerably reduced.

In addition to the high adsorption capacity for polar active substances such as nicotine, the nanoporous materials also have an affinity for less polar substances such as flavouring agents or essential oils. Flavouring agents of this type can be adsorbed separately or simultaneously on the respective substance, for example nicotine, and also released. In this connection, terpenes and terpenoids, in particular mono- and sesquiterpenes, as well as essential oils or solids such as mountain pine oil, eucalyptus oil, peppermint oil, clove oil, menthol, are of particular interest. Further, they have a high adsorption capacity for chemical or natural insect repellents such as p-menthane-3,8-diol. In addition, inhalable bronchospasmolytics for asthmatics such as salbutamol, formoterol, theophylline or terbutaline can be adsorbed into these materials.

Thus, combinations of active substances with preferred flavours or flavours which are significant for the respective application can be given off into the air or gas stream. As an example, the inhalate may be provided with a characteristic taste, or the air in an enclosed space may be enriched with a specific concentration of the substance.

According to one or more embodiments, pesticides, for example insecticides, acaricides or rodenticides or biologically active substances such as such as cinerin, jasmolin or pyrethrin, and also insect repellents such as p-menthanediol, diethyltoluamide (DEET) or permethrin can be stored in the depot material as an active substance and then released in a controlled manner with an appropriate dosing system. Other active substances to attract insects comprise the large group of pheromones, which can be dosed into the environmental air also using the system of the invention. One or more embodiments of the invention includes accommodating various active substances, flavouring agents or auxiliary materials, the interact of which together has a negative effect on the overall release, in various hybrid depots connected together one after the other, through which the air flows.

Figure 1:
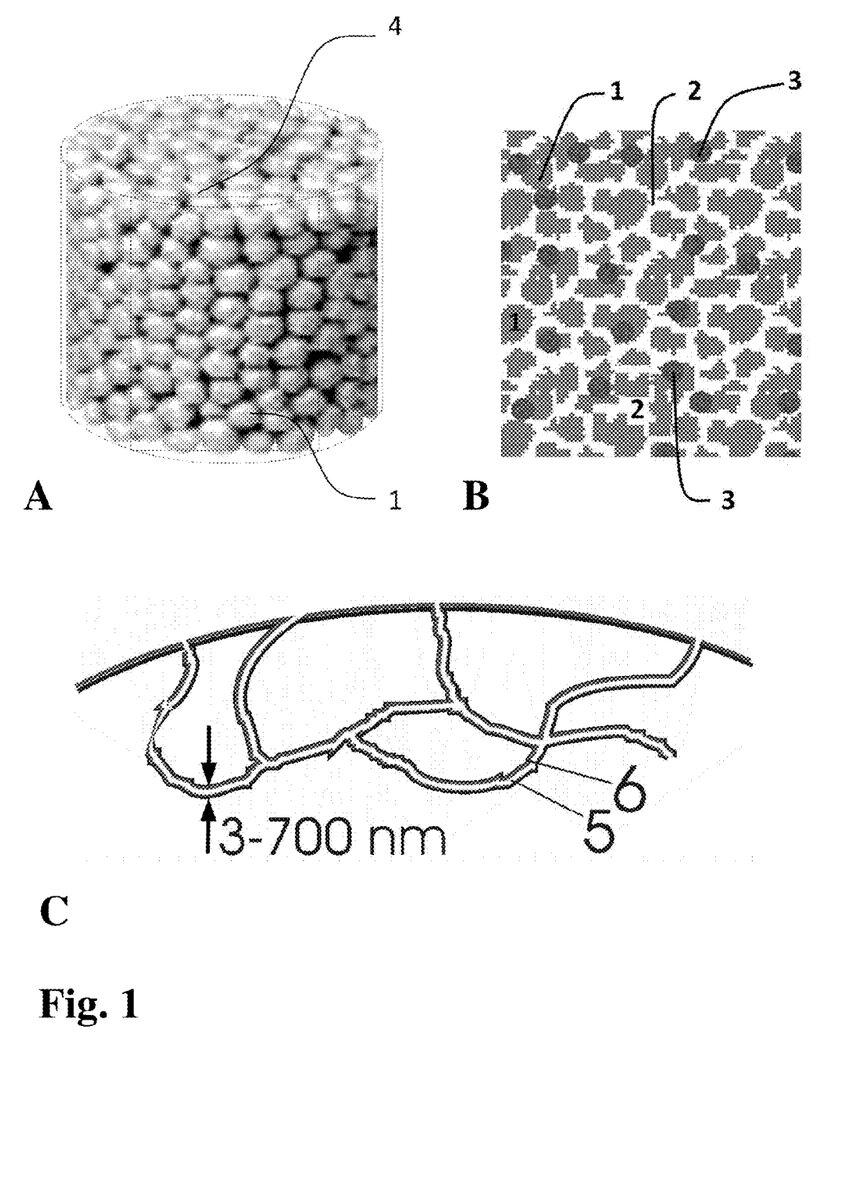
Figure 2:
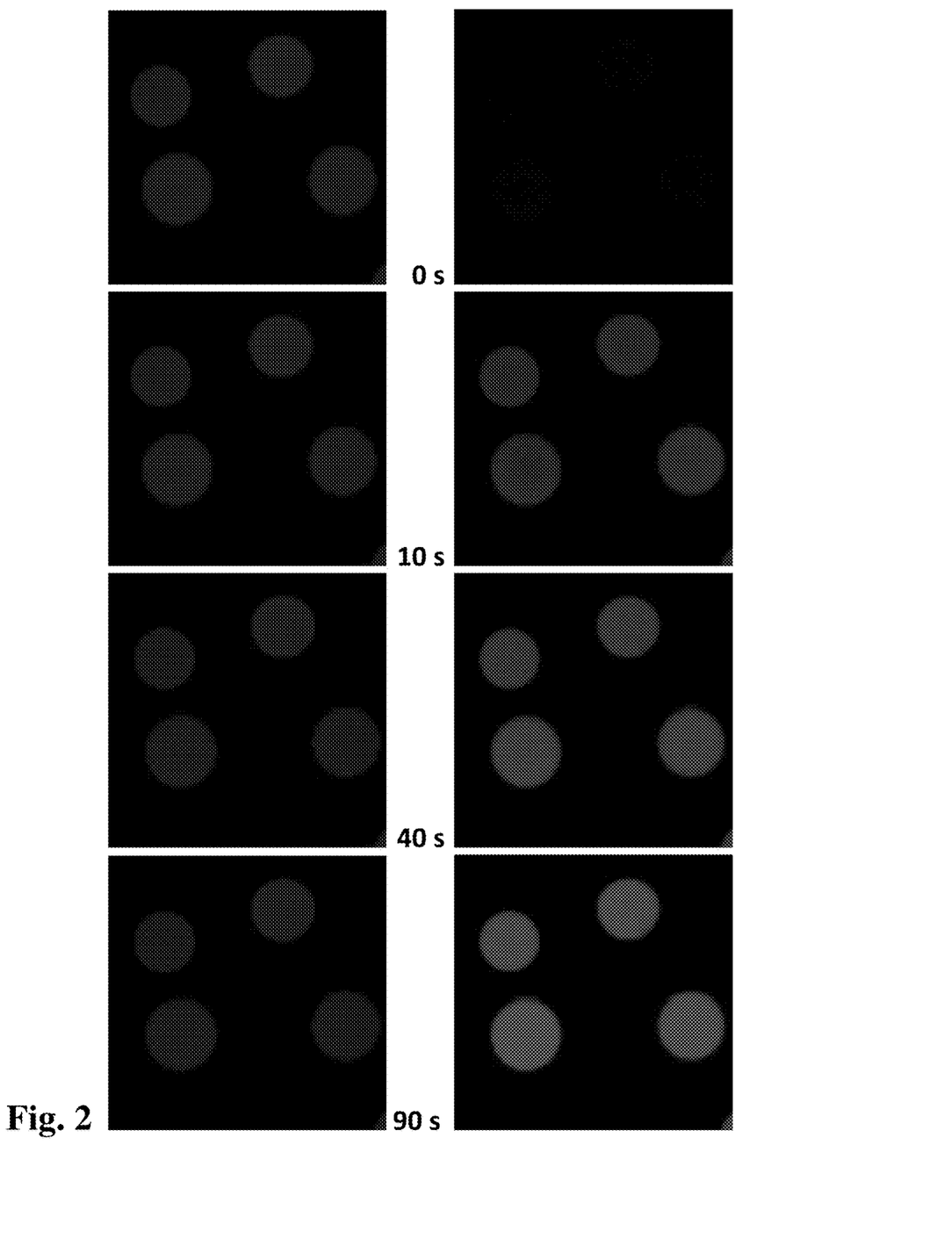
FIG. 2 shows the adsorption of rhodamine-polyallylamine in nanoporous particles.

FIG. 1 shows the diagrammatic construction of the depot for storing volatile active substances and/or flavouring agents: FIG. 1A shows a macroporous support matrix formed from sintered particles (1). The rectangle shown in dashed lines (4) diagrammatically shows a sectional plane through this sintered support matrix. FIG. 1B diagrammatically shows an enlarged view of the section (4) through the support matrix shown in FIG. 1A. Reference numeral (2) therein shows the pores, cavities and interstitial spaces of the particles (1) forming the support matrix. These pores, cavities and interstitial spaces (2) form a through network in which the nanoporous particles (3) are stably and permanently embedded or attached. FIG. 1C is a diagrammatic detailed view of a section through such a nanoporous particle (3). The nanoporous particle has pores (5) in the range 1 to 900 nm. At the surface of the nanoporous particles, in particular on the inner surface of the nanoporous particles formed by the pore walls, the active substance or flavouring agent (6) is adsorbed and is in constant exchange with the gas diffusing or flowing through the particle.

If such a depot is to be used for smokeless inhalation of an active substance such as nicotine, for example, then the depot can be matched to the size, shape and colour of a conventional cigarette filter. Similarly, the depot may be formed as a cartridge for accommodation in the head or shaft of a conventional tobacco pipe.

According to one or more, the depot may be fixed in a tube or a container with at least one inlet opening and at least one outlet opening, for example a cylinder. As an example, the container may be dimensioned such that it can be inserted into or attached to a smokeless cigarette, a smokeless cigarillo, a smokeless cigar or a smokeless tobacco pipe with the optical and haptic features of a cigarette or cigarillo, a cigar or a tobacco pipe.

The depot described here may on the one hand ensure the release of sufficient nicotine into the airways and on the other hand protect the nicotine from oxidation.

An average volume of 35 mL and a drag time for an average smoker of 1-2 seconds means that the contact time for the air flowing through the depot filter with the nicotine reservoir is very short. Transfer of the nicotine into the gas phase is approximately correlated with the contact area between the nicotine reservoir and the air.

The contact area of the adsorbed active substance on the nanoporous particles on the microporous support matrix available to the flowing air is very high in comparison with the contact area of the usual liquid-filled capillaries of absorbent material. In the latter, the evaporation surface area is only respective the accessible cross section (meniscus) of the filled capillaries, while in the case of the described depot, gas exchange can occur over the entire surface that is presenting the adsorbed active substance.

Tests regarding the adsorption of nitrogen molecules onto the surface of nanoporous materials of this type using the normal BET method show that their internal surface area can be more than 270 $m^2/g$. This is many times the effective external surface area of the non-porous nanopores which is disclosed, for example, in DE 10 2008 014 587 A1. With a nanoparticle diameter of approximately 100 nm, like that used in a number of embodiments of the cited document, the surface area is only 33 $m^2/g$.

Fixing the nanoporous particles on the surface of the macroporous support matrixes formed by sintering, for example, may be such that the nanopores of the fixed particles on the side facing away from the surface of the support matrix are not closed. Closing of these pores is even avoided when loading.

According to one or more embodiments, the nanoporous particles are not loaded by dropping in the pure liquid active substance such as nicotine. Loading is carried out after dissolving the active substance in a suitable, for example highly volatile organic solvent which, following complete evaporation of the active substance, is left in the depot. Examples of suitable solvents are pentane, hexane, heptane, acetone, ethanol, methanol or other highly volatile organic solvents. After evaporating off the solvent, the active substance, as desired, is adsorbed and fixed on the internal surface of the nanoporous particle without significantly preventing air from entering. In addition, the active substance is also present in the external surface area of the particle, whereas the internal surface prepared by the nanopores is larger than the outer surface area of the particle and the support matrix.

Nanoporous materials with a suitable affinity (pore surface area) for the active substance (flavouring agent) and adding a quantity of active substance (quantity of flavouring agent) in accordance with the loading or adsorption capacity of the nanoporous material thus on the one hand allows high loading of the depot with active substance or flavouring agents and on the other hand allows it to be rapidly released into a gas or gas mixture which flows through or by. Thus, transport of gas into the porous particles can be primarily by diffusion.

Loading of the depot with active substances and/or flavouring agents may advantageously be carried out after the sintering step. However, with stable active substances, it is possible to load the nanoporous particles during or prior to the sintering step.

A particular advantage of the nanoporous particles being permanently fixed on the surface of a macroporous support matrix by sintering, which nanoporous particles have a high specific surface area and affinity for active substances and flavouring agents, and their use in a depot for substance release into passing air lies in the fact that only the substances which have been bound therein are released. In the stream of air leaving the depot, in addition to the gaseous active substances and/or flavouring agents present, there are no droplets of liquid of any auxiliary materials or even of any particles that endanger health. Fixing the nanoporous particles onto the macroporous support matrix prevents the nanoporous particles from being torn out by the gas stream.

In order to modify the affinity of the nanoporous materials both intentionally in the direction of optimized uptake and also release, various possibilities are available for pretreating the pore surface, for example preliminary cleaning, activation, etching with acids or bases, and also silanization.

Surprisingly, simply coating the pores with polyelectrolytes using the layer-by-layer technique (LbL) has been shown to be particularly suitable in controlling uptake or release of active substances. The LbL coating of nanopores for functionalization thereof is disclosed in patent application DE 10 2004 013 637. As an example, it is possible to use this type of modification with polyelectrolyte layers to delay the release of active substances (see FIG. 6 and FIG. 7 in this regard).

According to one or more embodiments use the temperature dependency of the adsorption equilibrium of the active substances or the flavouring agents on the nanoporous particles. Thus, by adjusting the temperature of the flowing gas or gas mixture, for example air, the quantity of active substances and/or flavouring agents released into the passing volume can be adjusted. This adjustment of the released quantity of each substance can be made having regard to the requirements of the application in question. In addition to adjusting the affinity of the surface of the nanoporous particles for the active substances or flavouring agents, its release can also be adjusted using the temperature of the gas or gas mixture flowing through the depot. According to one or more embodiments, the release can also be adjusted using the temperature of the depot alone.

As an example, it is possible to use the heat released following an exothermic reaction to modulate the release kinetics of the active substance further. Equally, an electronically controlled heating element may be used to heat up the gas before passing it through the depot or to heat up the depot itself in order to adjust the quantity of active substance released.

According to one or more embodiments, the depot may be used in combination with an electrical, optical, chemical, physical or natural source of heat to pre-heat the gas or to heat up the depot, in order to increase the quantity of substance released or to control it. As an example, a smokeless cigarette may have a source of electrical heat.

According to one or more embodiments, the steps in the method for the manufacture of the depot for active substances and/or flavouring agents described herein comprises selecting a microparticulate matrix to embed nanoporous particulate materials; the selection of a nanoporous particulate material, specific adjustment of the affinity of the nanoparticulate materials by modification, co-sintering the nanoporous material with the support material at a temperature near to the melting point or softening point of the material used as the support matrix, and the adsorption of active substances and/or flavouring agents on the surface of the nanopores of the nanoporous material. This means that the quantity of adsorbed active substance can be specifically adjusted.

Inorganic materials such as glass, silicates or aluminosilicates, or thermoplastic organic polymers may be used as the matrix for fixing nanoporous particles.

According to one or more of embodiments, when selecting the nanoporous particulate material, the step for specifically adjusting the affinity for the active substance or flavouring agent may also be dispensed with. As discussed above, the co-sintering and adsorption or loading steps of the method may also be combined.

Nanoporous materials formed from silicon dioxide or aluminosilicates are currently produced in a wide variety of types.

According to one or more embodiments, a method for the manufacture of a depot is provided. The method concerns the manufacture of a hybrid structure comprising an open-pored macroporous support matrix through which a gas can flow and nanoporous particles immobilized on the support matrix, which particles contain at least one active substance to be released in their pores, wherein the support matrix consists of permanently interconnected particles or fibres.

According to one or more embodiments, a method for the manufacture of a depot is provided. The method concerns the manufacture of a hybrid structure comprising an open-pored macroporous support matrix through which a gas can flow and nanopores formed in the material of the support matrix, wherein the support matrix substantially or essentially consists of an inorganic material such as glass, silicates or aluminosilicates, and wherein the pores contain at least one releasable active substance.

According to one or more embodiments, the open-pored support matrix is manufactured by sintering microparticles. In accordance with a number of embodiments, the nanoporous particles are sintered together with the microparticles. In accordance with a number of embodiments, the nanopores are formed by leaching salts out of the material of the support matrix. In accordance with a number of embodiments, the at least one active substance or flavouring agent is adsorbed into the pores after forming the nanopores or immobilizing the nanoporous particles.

The following criteria may be applied when selecting the described depot:

1. Loading Capacity

A high loading capacity for the nanoporous materials is desirable for as small a depot volume as possible. The loading capacity here is given as a percentage by weight of the active substance over the weight of loaded particles.

Suitable loading capacities are in the range 20% to 90%, for example in the range 30% to 85%, in particular in the range 60% to 80%.

2. Releasability

In materials with a very high affinity for the active substance, the distribution coefficient between air and surface is very much in favour of the latter. As a result, the equilibrium concentration of the active substance in the air is low. In this case, the affinity for the active substances should be just sufficient to ensure effective adsorption. To adjust the interactions between the pore surface and the active substance, which determine the affinity, it is proposed that the nanoporous particles be pre-coated with polyelectrolytes using the LbL technique. Depending on the active substance, the complementary polyelectrolyte can be selected in order to present a cationic, anionic, hydrogen bond-forming or hydrophobic surface.

3. Size of Nanoporous Particles

This parameter significantly determines the design of the depot filter. If the nanoporous particles are too small, then if they are not sufficiently fixed and filtered, they can be ripped out and released from the depot and then, for example, enter the airways of the inhaling individual. If the particles are too large, the exchange of air with the active substance, for example nicotine, inside the particles is insufficient and the macropores of the support are blocked up. Examples of suitable size distributions for the nanoporous particles are 10 μm to 1 mm, in particular in the range 50 μm to 700 μm. Irregular particles with a narrow size distribution are particularly suitable.

4. Pore Width

The pore width of the nanoporous particles determines on the one hand the available surface area and thus the quantity of adsorbed active substance or flavouring agent, and on the other hand the rate of air exchange. Although reduced pore widths result in increased loading capacity, for example for nicotine, at the same time diffusive air exchange is reduced. When used in a depot, it is advantageous to use materials without too narrow a pore distribution. Pore diameters with a broad distribution in the range 1 nm to 900 nm, in particular in the range 3 nm to 700 nm, are suitable for effective adsorption. In this case, the inner surface area, measured by BET nitrogen adsorption, may be 30-1000 $m^2/g$, advantageously 100-600 $m^2/g$, for example.

5. Fixing the Nanoporous Particles in the Macroporous Matrix

In order to allow the gas or gas mixture, for example air, to flow smoothly through the nanoporous particles containing the active substance but to prevent the particles from getting into air that might have been breathed in, they should be stably fixed in the depot. In an advantageous embodiment of a depot, the nanoporous particles, which only melt at higher temperatures, are co-sintered with larger sinter granulates formed from polymers which have a lower melting point or softening point. The proportion of nanoporous particles in the sintered part may in particular be in the range 2% to 40%, for example in the range 5% to 20%. The proportion of nanoporous particles should in this regard be selected so that the sintered or fused support matrix is still sufficiently stable mechanically. As an example, proportions of nanoporous particles of greater than 40% would in some cases no longer provide the macroporous support matrix with sufficient integrity.

A model experiment can be used to demonstrate that the internal pores of immobilized particles are accessible by smaller molecules, in particular air.

Nanoporous particles were incubated with Cy5-labelled polymer. The polymer penetrated completely into the pores and was adsorbed onto its surface. A confocal microscope then showed that the low molecular weight fluorescent dye sulphorhodamine penetrated quickly into these pores without displacing the other dye (see FIG. 2).

The left hand column in FIG. 2 shows the sectional image, taken in the Cy5 channel of a confocal fluorescence microscope with a zoom factor of 4 and an amplifying voltage for the photomultiplier of 570 V of the nanoporous particle (diameter 10 μm) with the polymer firmly attached to the internal surface of the pores, while the right hand column of the image shows the rhodamine channel, with a zoom factor of 4 and with a photomultiplier voltage of 740 V. The incubation time given (seconds) shows the penetration of a $10^{-5}$ M solution of the fluorescent dye sulphorhodamine into the pores of the particle. After 10 s, the particles were already completely loaded with sulphorhodamine right into the interior, and there is almost no radial gradient. This means that even the interior of the particle is accessible without major inhibition to diffusion. The original image size was 40 μm×40 μm.

This means that in contrast to a liquid which is drawn into the micropores by capillary action, the nanopores are not enclosed by an adsorbed layer. Gas molecules, for example air, can also readily enter and leave by diffusion or convection; this is essential for rapid exchange of active substances.

In accordance with a number of embodiments, in order to combine macro- with nanoporosity, silica beads with a size range of 50 μm to 1000 μm, for example in the range 100 μm to 700 μm, are sintered together and are rendered nanoporous in subsequent steps by leaching with salts. Suitable techniques are set out in the specialist literature.

One or more embodiments of the depot are based on the release of active substances or flavouring agents from their salts. Thus, for example, ammonium carbonate might be immobilized in a first depot, releasing ammonia when air flows through it. If a further, downstream, depot holds a salt of the active substance, for example nicotine acetate, then reaction with the ammonia will release the free, volatile nicotine base. An ammonia-releasing depot may also be used in another embodiment as a pre-filter for a hybrid depot of free nicotine so that irritation of the mouth and throat on inhalation of the free nicotine base is reduced by the ammonia. This effect is employed in normal cigarettes.

In accordance with a number of embodiments, at least two depots may be arranged one behind the other and loaded with different substances. The subsequently arranged depots may, for example, be "daisy-chained" in a cartridge.

Examples of embodiments will now be described with reference to the accompanying drawings.

First Example 20 mg of nanoporous spherical chromatographic support particles with an inner (BET) specific surface area of 600 $m^2/g$ and a diameter of 10 μm and a narrow pore size distribution with a pore diameter of 12 nm was intimately mixed with 80 mg of polyethylene beads with a diameter of 500 μm, transferred into a mould prepared from a glass tube and sintered for 15 min at 118° C. This resulted in a hybrid filter depot with a diameter of 6 mm and a thickness of 9 mm. The depot was loaded with 6 mg of nicotine by dissolving the nicotine in 0.5 mL of ethanol and applying it to the depot which was in a small cylindrical container. After complete evaporation of the ethanol, 35 mL of air heated to 60° C. was drawn through the depot in 1-2 seconds. The quantity of nicotine in the drawn air was then determined.

This was accomplished by solvent extraction with 0.1 M hydrochloric acid and then by spectroscopic analysis ($\epsilon_{259nm,pH1}$=4040 L/mol·cm).

Figure 3:
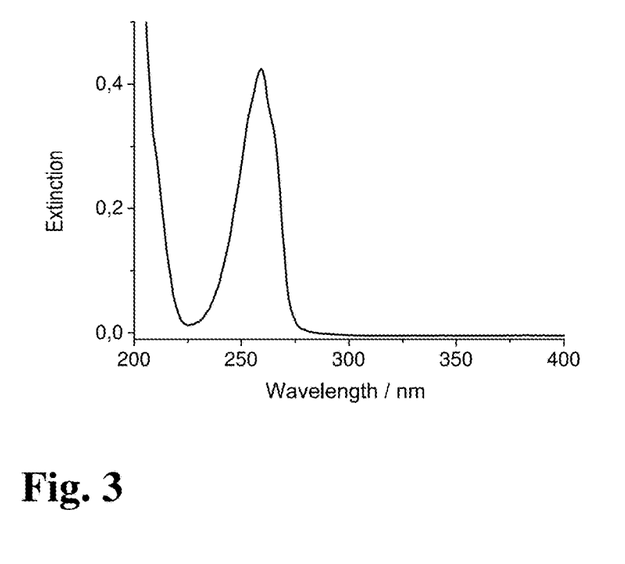
FIG. 3 shows the spectroscopic analysis of nicotine according to Example 1.

FIG. 3 shows the UV/vis absorption spectrum for 0.107 mM nicotine in 0.1 M hydrochloric acid. The nicotine content of the air drawn through the depot is largely constant at 1.15 mg/L for the first 15 drags.

Second Example nanoporous spherical particles of a magnesium aluminosilicate with a diameter of 50 μm to 150 μm and a pore width distribution in the range 5 nm to 300 nm were sintered with polyethylene beads into a macroporous depot with a diameter of 5.7 mm and a thickness of 3 mm. Fixing was accomplished by co-sintering with polyethylene beads with a dimension of 500 μm for 15 minutes at 118° C. Microscopic imaging of the stable conglomerate obtained showed the macroporous depot with embedded nanoporous particles (see FIG. 4).

Figure 4:
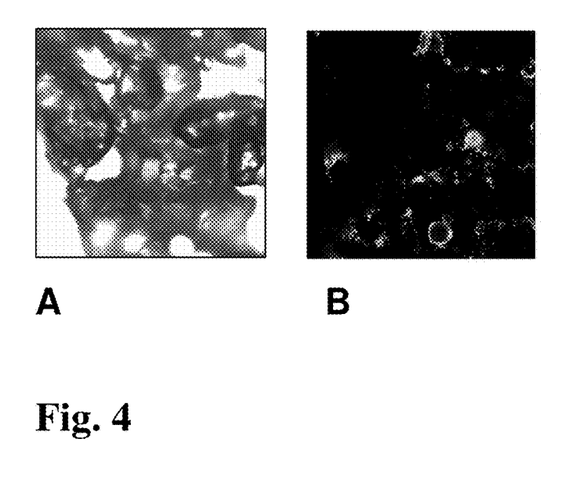
FIG. 4A—transmitted light mode. The approximately 200 μm channels in the macroporous matrix can easily be seen.
FIG. 4B—confocal fluorescence imaging of the embedded aluminosilicate particles, which have been selectively dyed with rhodamine 6G (image size 1 mm×1 mm).

FIG. 4 shows the microscope images for the sintered hybrid filter depot. A—transmitted light mode. The approximately 200 μm channels in the macroporous matrix can easily be seen. B—confocal fluorescence imaging of the embedded aluminosilicate particles, which have been selectively dyed with rhodamine 6G (image size 1 mm×1 mm).

A proportion by weight of 31.5 mg of polyethylene and 3.2 mg of nanoporous particles was selected, which was suitable for subsequent loading with 5 mg of nicotine. The nicotine was primarily deposited in the nanoporous particles. The depot was substantially colourless following loading. 35 mL of air at 60° C. was drawn through this depot over the duration of a normal drag by a smoker. The nicotine content of the air drawn through the depot was 1.4 mg/L.

Third Example nanoporous spherical particles of a precipitated silica with a mean diameter of 100 μm and an internal (BET) specific surface area of 150-300 m²/g and a particularly broad pore width distribution in the range 3 nm to 700 nm were used to produce a depot filter. Fixing was carried out as described in the second example. 5.2 mg of the nanoporous particles were sintered with 31.5 mg of polyethylene beads; this was sufficient for loading with 10 mg of nicotine. 35 mL of air at ambient temperature was drawn through this depot over the duration of a normal drag by a smoker and the nicotine content in the air that had been drawn through was determined for 15 successive drags (see FIG. 5).

Figure 5:
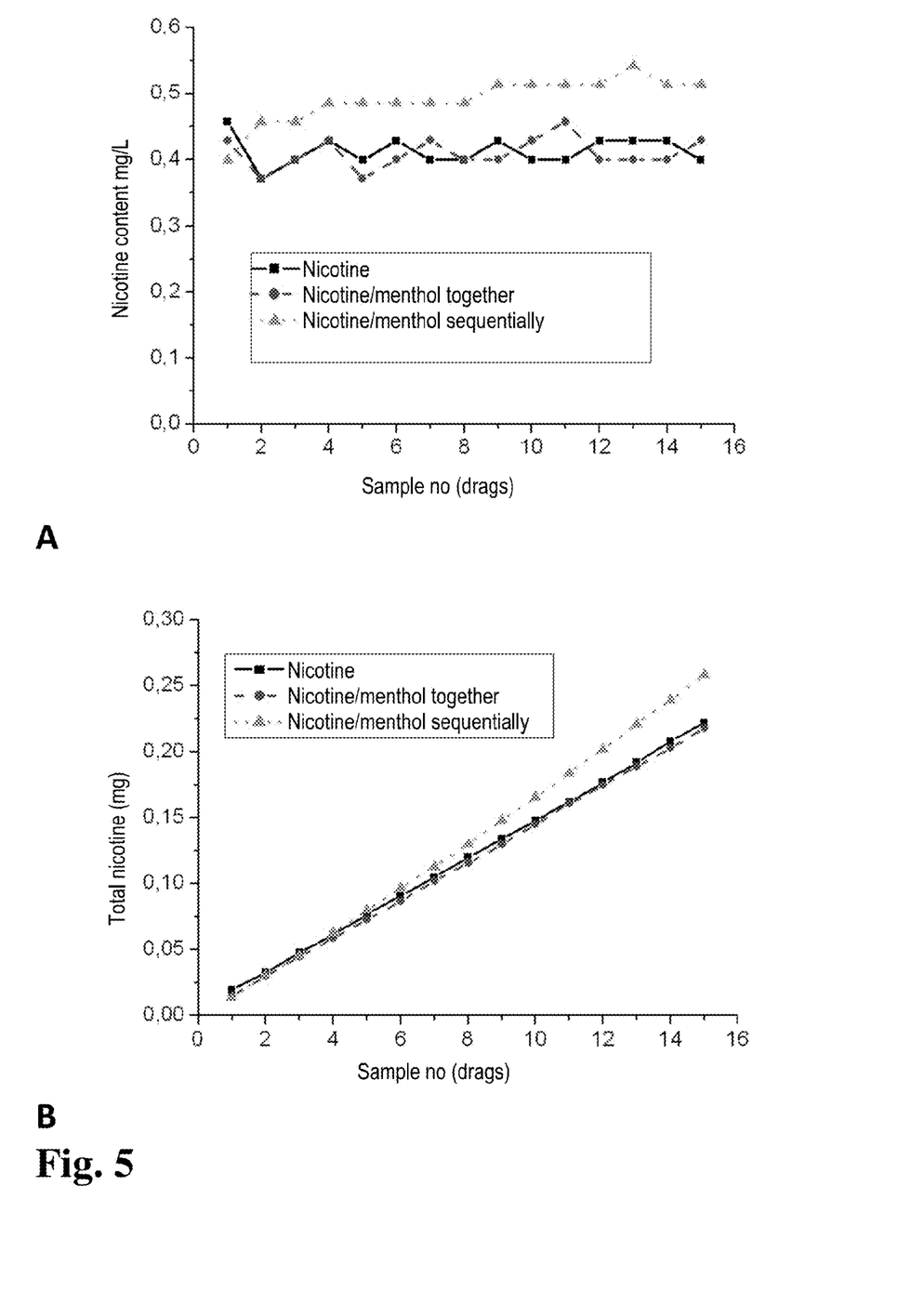
FIG. 5A—individual measurements, nicotine content of drawn air.
FIG. 5B—cumulative value for release of nicotine. The line (square data points) shows the corresponding curve for loading with 10 mg of nicotine.

FIG. 5 shows the nicotine released per inhalation (35 mL) drag of air. A—individual measurements, nicotine content of drawn air; B—cumulative value for release of nicotine. The line (square data points) shows the corresponding curve for loading with 10 mg of nicotine.

In that number of normal cigarette drags, the quantity of nicotine released in the drawn air was substantially the same, indicating a highly reliable nicotine release readily adjustable through the quantity of sintered particles. The experiment was carried out on 3 depots produced in the same manner and each draw produced almost identical values of approximately 0.4 mg/L. According to DIN ISO 3308:2000-12, drags each of 35 mL when smoking a cigarette corresponds to a total quantity of 0.22 mg of nicotine. This value for the inhaled nicotine quantity corresponds to a very light cigarette.

Fourth Example

A depot filter according to Example 3 was also loaded with 1 mg of menthol as well as with 10 mg of nicotine. The air inhaled through this depot had a strong menthol flavour, comparable to a menthol cigarette, for example. 35 mL of air at room temperature was drawn through this depot 15 times over the duration of a normal drag by a smoker and an identical nicotine release as in the case of the third example was measured (see FIG. 5). The dashed line (circular data points) shows the curve for simultaneously loading 10 mg of nicotine and 1 mg of menthol in one depot.

Fifth Example a dual filter system was produced with 1 mg of menthol in one depot filter in accordance with Example 3 and 10 mg of nicotine in a further downstream depot in accordance with Example 3. The air inhaled through this depot combination had a strong menthol flavour, comparable to a menthol cigarette, for example. 35 mL of air at room temperature was drawn through this depot 15 times over the duration of a normal drag by a smoker and a somewhat higher release of nicotine was measured than in the case of the third and fourth exemplary embodiments (see FIG. 5). The dotted line (triangular data points) shows the curve for the dual depot system. Clearly, synergistic effects between different released substances can be exploited to obtain even greater releases than with the release of individual substances.

Sixth Example the nanoporous particles in a depot in accordance with Example 3 were coated prior to filling with polyallylamine (PAH)/polystyrene sulphonate (PSS) or polyallylamine (PAH)/polymethacrylate (PMAA) in order to increase the negative charge on the surface and thus the affinity for nicotine or to reduce the release rate. After loading with 10 mg of nicotine, release was tested at room temperature; it was much lower for the coated particles for the same loading (see FIG. 6).

Figure 6:
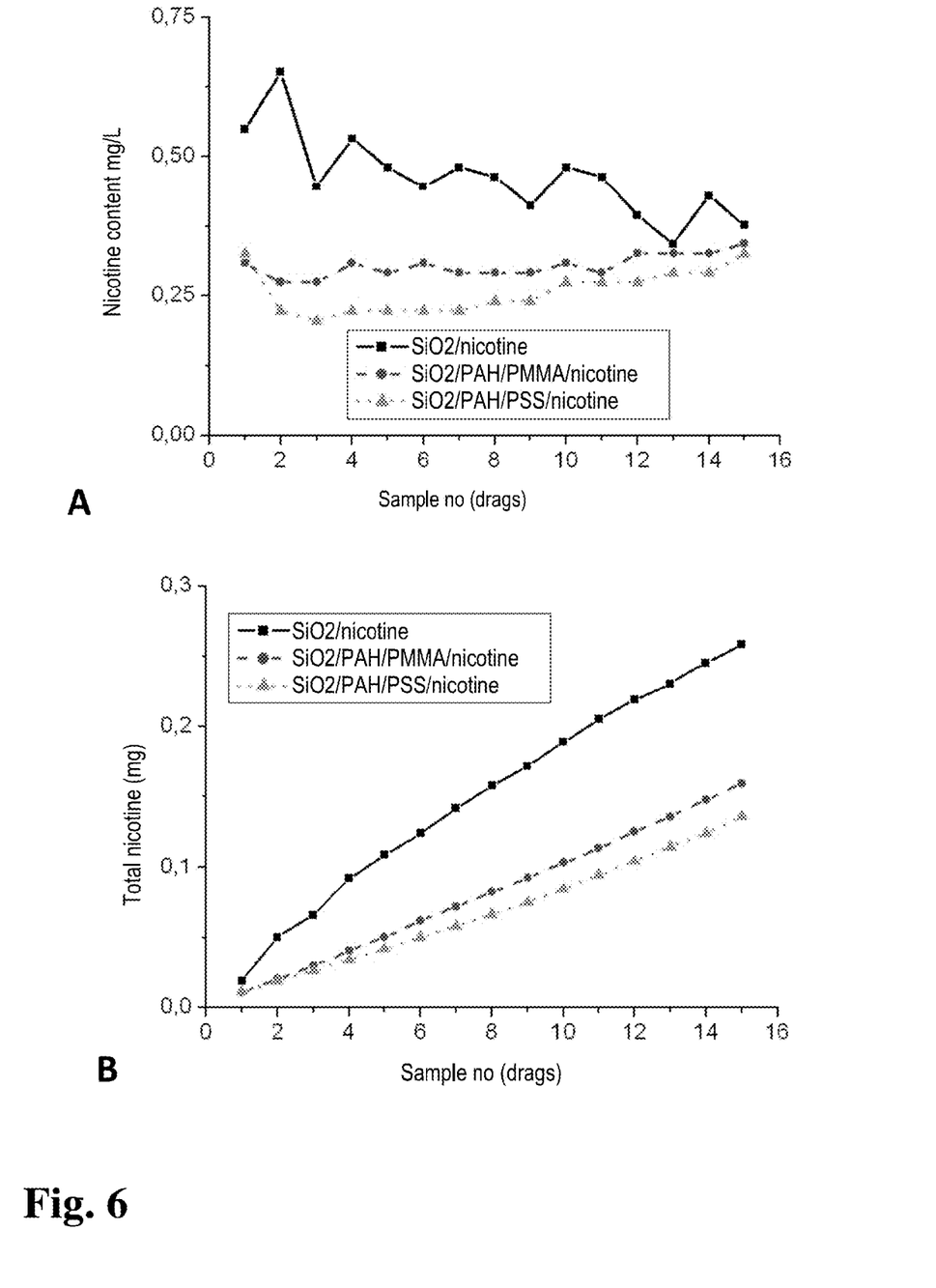
Figure 7:
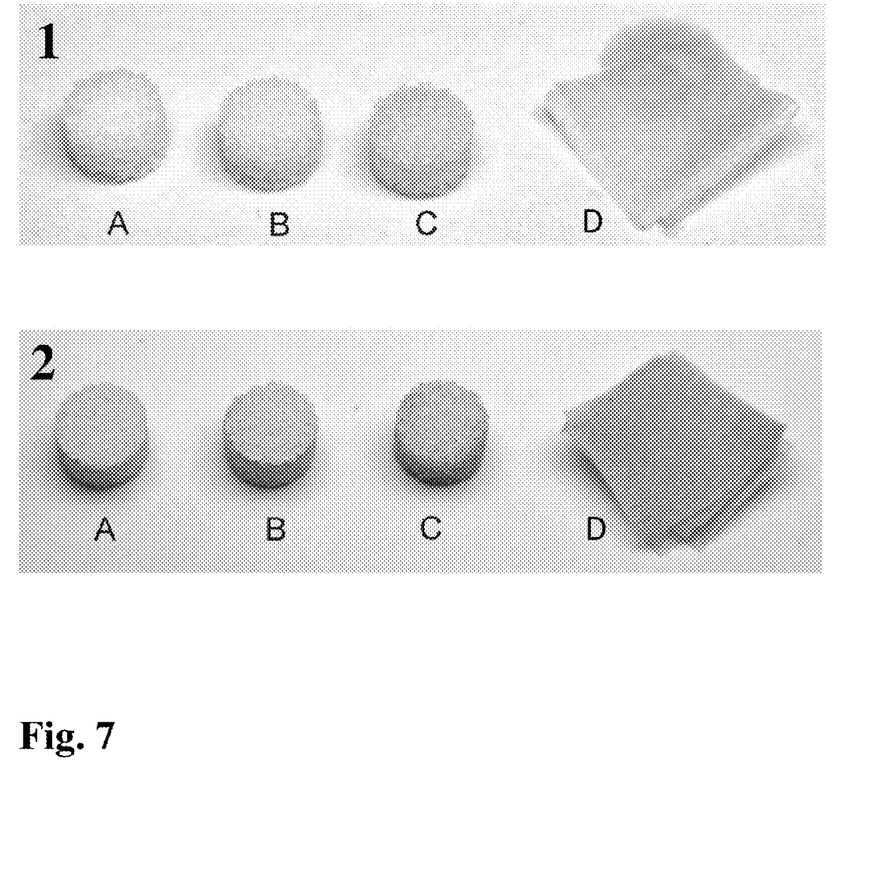

FIG. 6 shows the measured release of nicotine per inhaled drag of 35 mL of air. FIG. 6A shows individual measurements; FIG. 6B shows the cumulative release. The line drawn through them (square data points) shows the measured release of nicotine for a nicotine load of 10 mg through unmodified nanoporous particles. The dashed line (circular data points) shows the measured release of nicotine for a load of 10 mg of nicotine through particles with pores coated with poly(allylamine) (PAH) and then with poly(methacrylic acid) (PMAA). The dotted line (triangular data points) shows the path of the measured release of nicotine after increasing the affinity of the nanoporous particles for nicotine using the LbL coating described in Example 6 with poly(allylamine)/poly(styrene sulphonate) for a 10 mg nicotine charge.

Seventh Example stability test: depots were produced in accordance with Example 3 and loaded with different quantities of nicotine (A: 8 mg, B: 10 mg and C: 12 mg). for comparison, 10 mg of nicotine was applied to an acetate fibre paper (D). The upper row in FIG. 7 (image 1) shows the samples immediately after loading with nicotine.

These samples were then stored in a sealed container for 48 h at 60° C. The lower row in FIG. 7 (image 2) shows the depots after storing under the given stress conditions, which were comparable with storing at room temperature for several months. As can clearly be seen, the nicotine on the acetate paper has browned significantly. Depots A and B have only become slightly coloured by the decomposition products, whereas depot C also displays a strong yellow/brown coloration. It is clear that the takeup capacity of the nanoporous material in the depot is exhausted for a quantity of 10 mg nicotine and thus free nicotine has also been deposited outside the particles in the macroporous polyethylene matrix.

Eighth Example

Two depots were produced in accordance with Example 3. One of the depots was loaded with 10 mg of eucalyptus oil in methanol; the other was loaded with 10 mg of mountain pine oil in cyclohexane. The depots were each positioned in a support tube and then air was passed through at room temperature and at a moderate speed. The downstream air was introduced into a 20 L canister. Despite the large volume of air, in both cases an intense eucalyptus or mountain pine oil fragrance was detected.

Figure 8:
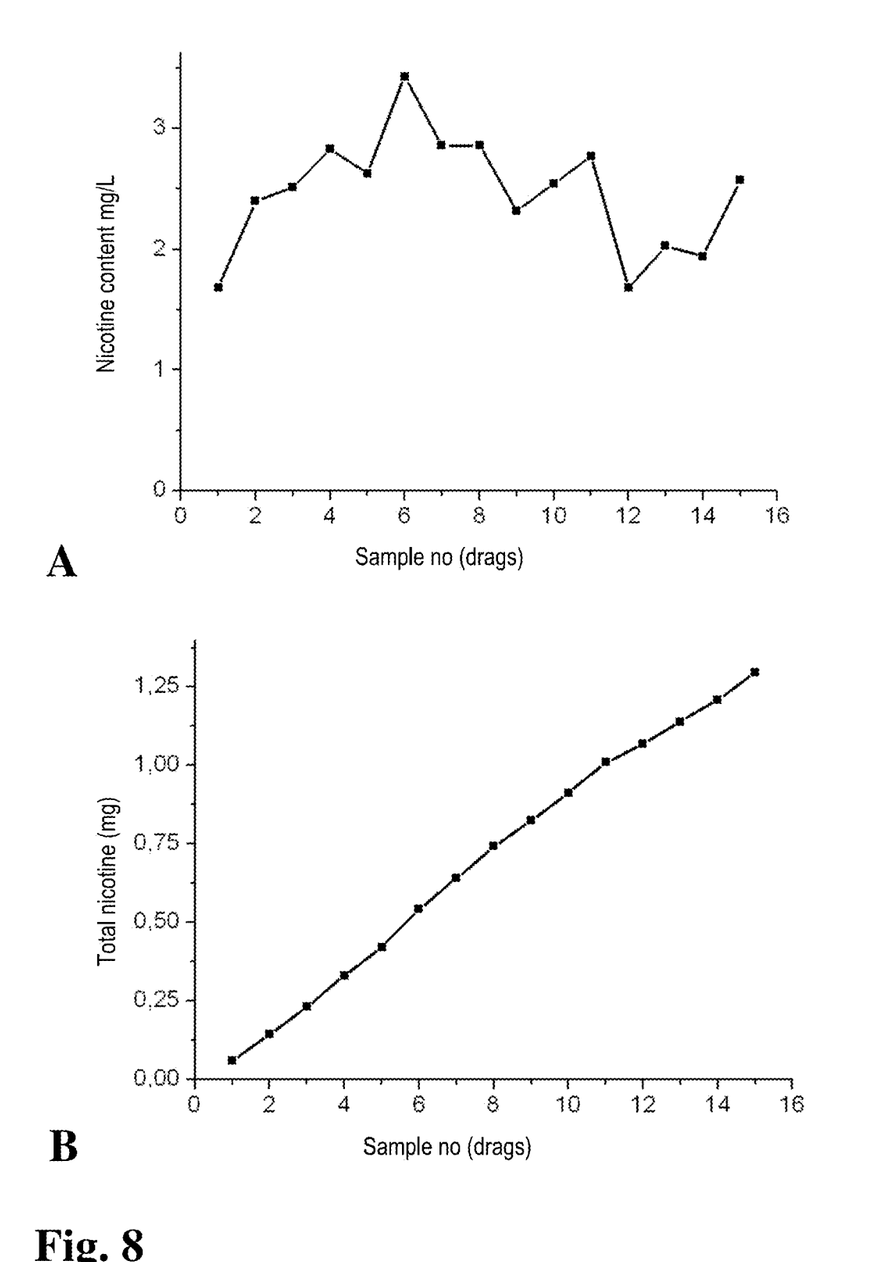
FIG. 8A. shows the nicotine content of the drawn air (drags)
FIG. 8B. shows the total nicotine content after 15 drags.

Ninth Example nanoporous spherical particles with a precipitated silica with a diameter of 50 μm and an internal (BET) specific surface area of 150-300 m²/g and a pore width distribution in the range 3 nm to 700 nm and an average adsorption capacity were used to produce a depot filter. Fixing was accomplished as described in the second example. 5.2 mg of the nanoporous particles were sintered with 31.5 mg of polyethylene beads, which was sufficient for a loading of 10 mg of nicotine. 15×35 mL of air was drawn through this depot in the duration of a normal drag by a smoker. The air was heated to approximately 60-80° C. using an upstream heating element and the nicotine content of the drawn air was determined (see FIG. 8A). The release in this case was highly irregular, since the temperature varied substantially. The total nicotine content after 15 drags (see FIG. 8B) was 1.3 mg, which corresponded to the nicotine content of a very strong cigarette.

Tenth Example

Figure 9:
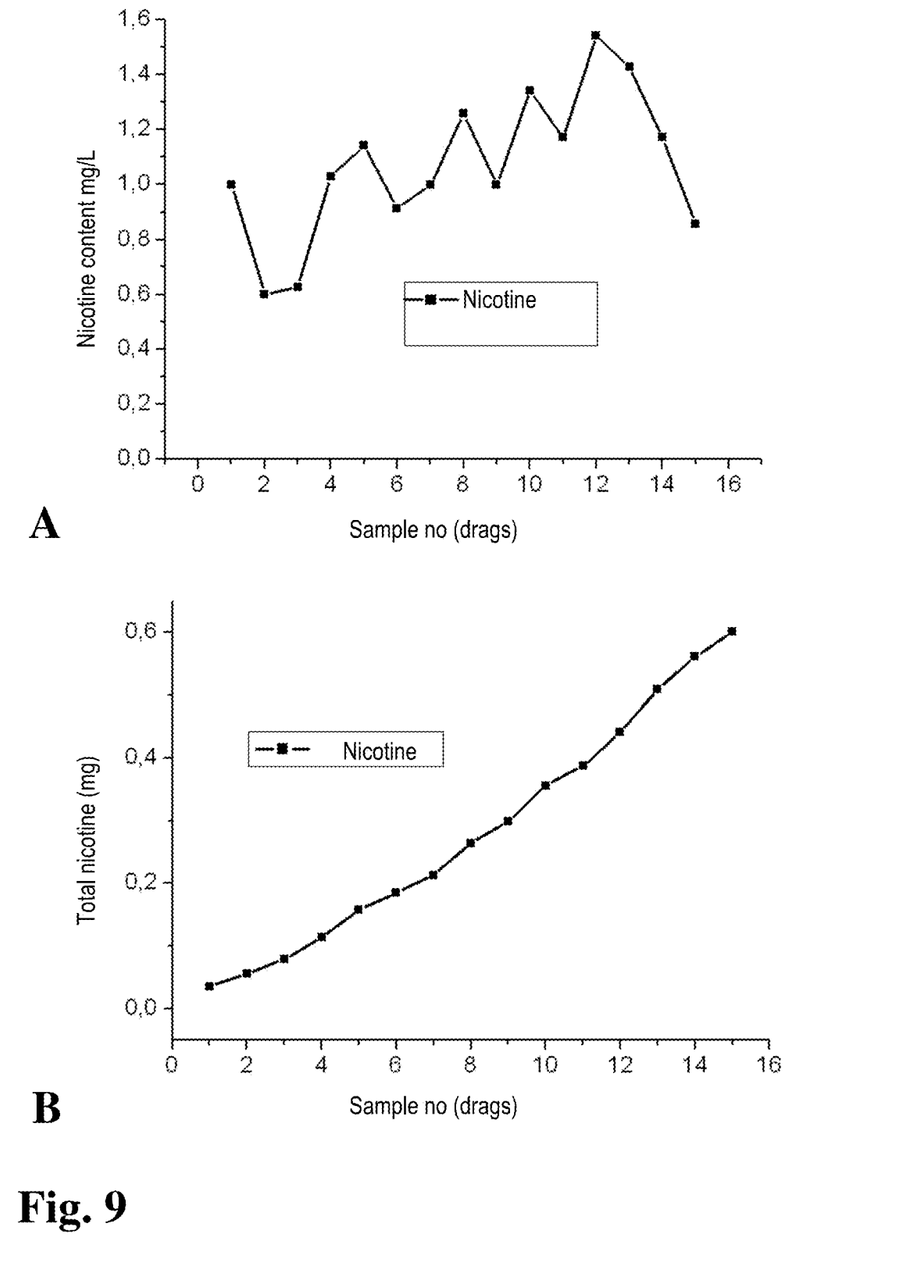
FIG. 9A. shows the nicotine content of the drawn air (drags)
FIG. 9B. shows the total nicotine content after 15 drags.

Glass beads with a dimension of 300 μm to 500 μm formed from an alkali borosilicate glass were sintered into a macroporous matrix cylinder with a diameter of 6 mm and a height of 8 mm. After phase separation in the glass at temperatures between 400° C. and 600° C., the soluble borate phase was leached out under acidic conditions to produce nanoporosity in the beads. Subsequent basic leaching produced pores that were permeable to active substances or air. The hybrid depot obtained was loaded with 10 mg of nicotine and its release in drawn air at a temperature of 60° C. was determined for 15 drags each of 35 mL. The air in this case had been pre-heated in a water bath and thus was at a substantially constant temperature. In the 15 drags, a slightly increasing concentration of nicotine from 0.8 to 1.3 mg/l was measured (see FIG. 9).

The present invention has been illustrated by means of exemplary embodiments. These exemplary embodiments should in no way be understood to limit the present invention. The claims below constitute a first non-binding approach to describing the invention in general terms.

REFERENCES

WO 2004/098324
WO 2004/095955
CN 101268867A (WO 2009/105919)
DE 10 2008 014 587
DE 10 2005 054 255 A1
DE 103 56 925 B4
WO 2006/002 445 A2
AT 505 472 A1
DE 10 2004 013 637
C Peyratout, L Dahne (2004) "Tailor-made polyelectrolyte microcapsules: from multilayers to smart containers" Review in *Angew Chem Int Ed* 43, 3762-3783.
F Janowski, D Enke (2002) "Porous glasses" in: Handbook of porous solids (F Schüth, K S W Sing, J Weitkamp—Eds), volume 3, Wiley-VCH, Weinheim 2002, 1432.
D Enke, F Janowski, W Schwieger (2003) "Porous glasses in the 21$^{st}$ century—a short review" Microporous and Mesoporous Materials, 60, 19-30.
DIN ISO 3308: 2000-12 (cigarette smoking machines for routine analyses—terms and standard conditions).
DIN ISO 9277: 2003-05 (determination of specific surface area of solids by gas adsorption using the BET method).

LIST OF REFERENCE NUMERALS

1—particle of support matrix
2—pores and cavities in support matrix
3—nanoporous particle
4—diagrammatic sectional plane through the support matrix
5—pores of nanoporous particle
6—adsorbed active substance

The invention claimed is:

1. A depot for storing and releasing a substance into a gas phase, comprising a hybrid structure formed from:
    an open-pored macroporous support matrix through which a gas can flow; and
    nanoporous particles immobilized on the support matrix which contain at least one releasable substance in their pores;
    wherein the support matrix is comprised of permanently interconnected particles or fibres.

2. The depot as claimed in claim 1, wherein the nanoporous particles consist of a material other than that of the support matrix.

3. A depot for storing and releasing a substance into a gas phase, comprising a hybrid structure formed from:
    an open-pored macroporous support matrix through which a gas can flow; and
    nanopores formed in the material of the support matrix;
    wherein the support matrix substantially consists of an inorganic material such as glass, silicates or aluminosilicates and wherein the pores contain at least one substance to be released.

4. The depot as claimed in one of claims 1 to 3, wherein the substance is a pharmaceutically active substance or a flavouring agent which is adsorbed onto or fixed in the pores.

5. The depot as claimed in one of claims 1 to 3, wherein the substance is nicotine, a nicotine salt or a component of cigars or cigarette tobacco, which is adsorbed onto or fixed in the pores.

6. The depot as claimed in one of claims 1 to 3, wherein the substance is an insecticide, an acaricide or a rodenticide, or a biologically active substance such as cinerin, jasmolin or pyrethrin, or a repellent to repel pets or wild animals or an insect repellent such as pmenthane-diol, diethyltoluamide or permethrin and is adsorbed onto or fixed in the pores.

7. The depot as claimed in one of claims 1 to 3, wherein the substance is a pheromone to attract insects.

8. A cartridge for a dosing device, comprising:
- a cylinder, wherein the cylinder has at least one inlet opening and at least one outlet opening;
- a depot as claimed in any one of the claims 1-3, wherein the depot is held in the cylinder between the inlet and outlet opening.

9. A smokeless cigarette, cigarillo, cigar or tobacco pipe comprising a base unit and at least one depot as claimed in one of claims 1 to 3 disposed in the base unit, wherein the substance is nicotine, a nicotine salt, a nicotine derivative or a component of cigar or cigarette tobacco, which is adsorbed onto or fixed in the pores.

10. The smokeless cigarette, cigarillo, cigar or tobacco pipe as claimed in claim 9, wherein the cigarette, cigarillo, cigar or tobacco pipe has a heat source to pre-heat the gas or to heat the depot.

11. A device adapted to release a substance into a stream of gas, comprising a depot as claimed in one of claims 1 to 3, or a cartridge as claimed in claim 8, wherein the stream of gas can be conducted through the depot.

* * * * *